（12）United States Patent
Buxbaum et al.

(10) Patent No.: US 9,735,066 B2
(45) Date of Patent: Aug. 15, 2017

(54) SURFACE DELAYERING WITH A PROGRAMMED MANIPULATOR

(71) Applicant: FEI Company, Hillsboro, OR (US)

(72) Inventors: Alexander Buxbaum, Portland, OR (US); Michael Schmidt, Gresham, OR (US)

(73) Assignee: FEI Company, Hillsboro, OR (US)

( * ) Notice: Subject to any disclaimer, the term of this patent is extended or adjusted under 35 U.S.C. 154(b) by 203 days.

(21) Appl. No.: 14/169,100

(22) Filed: Jan. 30, 2014

(65) Prior Publication Data

US 2015/0214124 A1  Jul. 30, 2015

(51) Int. Cl.
| | |
|---|---|
| *H01L 21/66* | (2006.01) |
| *H01L 21/67* | (2006.01) |
| *B28D 5/04* | (2006.01) |
| *G03F 1/72* | (2012.01) |
| *G03F 7/20* | (2006.01) |
| *H01L 21/304* | (2006.01) |
| *G01N 1/28* | (2006.01) |
| *B26D 3/28* | (2006.01) |
| *G03F 1/84* | (2012.01) |

(52) U.S. Cl.
CPC ............. *H01L 22/14* (2013.01); *B26D 3/282* (2013.01); *B28D 5/04* (2013.01); *G01N 1/286* (2013.01); *G03F 1/72* (2013.01); *G03F 1/84* (2013.01); *G03F 7/7065* (2013.01); *G03F 7/70608* (2013.01); *H01L 21/304* (2013.01); *G01N 2001/2873* (2013.01); *Y10T 156/1967* (2015.01)

(58) Field of Classification Search
None
See application file for complete search history.

(56) References Cited

U.S. PATENT DOCUMENTS

| | | | |
|---|---|---|---|
| 6,352,454 B1 * | 3/2002 | Kim | G01R 1/07342 200/242 |
| 6,353,219 B1 | 3/2002 | Kley | |
| 7,375,324 B2 | 5/2008 | Linder et al. | |
| 8,334,512 B2 | 12/2012 | Luecken et al. | |
| 2003/0017649 A1 | 1/2003 | Rubin | |

(Continued)

OTHER PUBLICATIONS

Egerton, R. F., "Electron energy-loss spectroscopy in the TEM," Reports on Progress in Physics, 2009, pp. 1-25, vol. 72.

*Primary Examiner* — Calvin Choi
*Assistant Examiner* — Xiamong Liu
(74) *Attorney, Agent, or Firm* — Scheinberg & Associates, P.C.; Michael O. Scheinberg

(57) ABSTRACT

A method and apparatus for use in surface delayering for fault isolation and defect localization of a sample work piece is provided. More particularly, a method and apparatus for mechanically peeling of one or more layers from the sample in a rapid, controlled, and accurate manner is provided. A programmable actuator includes a delayering probe tip with a cutting edge that is shaped to quickly and accurately peel away a layer of material from a sample. The cutting face of the delayering probe tip is configured so that each peeling step peels away an area of material having a linear dimension substantially equal to the linear dimension of the delayering probe tip cutting face. The surface delayering may take place inside a vacuum chamber so that the target area of the sample can be observed in-situ with FIB/SEM imaging.

17 Claims, 6 Drawing Sheets

(56) References Cited

U.S. PATENT DOCUMENTS

| | | | |
|---|---|---|---|
| 2003/0098700 A1* | 5/2003 | Yoshida | G01R 1/06738 324/754.2 |
| 2004/0119463 A1* | 6/2004 | Lou | G01R 1/07342 324/750.08 |
| 2004/0126995 A1 | 7/2004 | Ohno et al. | |
| 2005/0139781 A1* | 6/2005 | Hazaki | G01N 23/225 250/442.11 |
| 2005/0285033 A1* | 12/2005 | Takaoka | G01N 23/00 250/309 |
| 2006/0147814 A1 | 7/2006 | Liang | |
| 2008/0081267 A1 | 4/2008 | Sim et al. | |
| 2008/0107970 A1 | 5/2008 | Tanabe et al. | |
| 2008/0107975 A1 | 5/2008 | Takaoka et al. | |
| 2008/0143369 A1* | 6/2008 | Narita | G01R 1/07342 324/755.07 |
| 2011/0095766 A1* | 4/2011 | Ogle | G11B 19/048 324/537 |
| 2013/0047302 A1 | 2/2013 | Noel et al. | |

\* cited by examiner

SURFACE DELAYERING WITH A PROGRAMMED MANIPULATOR

TECHNICAL FIELD OF THE INVENTION

The present invention relates to a method and apparatus for surface delayering of a sample work piece for fault isolation and defect localization.

BACKGROUND OF THE INVENTION

There is a demand in the semiconductor industry to produce semiconductor wafers with higher device densities. Such high densities require that the dimensions of the device be scaled down requiring smaller and smaller feature sizes. For example, semiconductor wafers are typically composed of different interconnected layers and the width and spacing of interconnecting lines must necessarily be closer and closer together.

Failure of the semiconductor wafer sometimes occurs due to various physical, chemical, or mechanical problems. For example, failure may occur due to electrical overstress, contamination, or wear out. When there is a failure it is important to perform an analysis for to find where and why the device fails. Before fault analysis can be performed the sample must be prepared to isolate and expose the fault for analysis. This process is typically known as fault isolation. The fault isolation process can be performed using known methods, such as, for example, electrical probing and active or passive voltage contrast on uniform surfaces at a target area or the region of the defective circuit or fault. The target area is generally the location believed to be the cause of the failure.

Fault analysis using electrical probing typically includes moving a probe into contact with an electrical circuit on a surface of a sample and applying a voltage or current. One important process in fault isolation using electrical probing includes removing material from the sample surface one layer at a time at or near the target area so that each layer can be sequentially inspected by known voltage contrast methods or probed so that the failure can be isolated and analyzed. It is important to have a clean uniform surface to provide a good electrical or ohmic contact between the probe and the electrical circuit in order to measure the desired electrical property of the circuit. Inspection of the target area can be done using a scanning electron microscope (SEM) or other inspection methods, such as, for example, ion beam imaging. Inspection of the target area typically requires a controlled environment in which the sample is place within a controlled environment, such as, for example, a vacuum chamber.

The process of surface removal by layer is generally referred to as surface delayering. Known methods of delayering are time consuming, difficult, and often result in a sample surface on which it is difficult to perform any fault analysis. Delayering is even more difficult when the target area is located beneath one or more layers and becomes more difficult as the layers become increasingly thinner.

Most current methods of delayering are ex-situ. That is, the methods are performed outside of the SEM vacuum chamber. For example, the sample is removed from the vacuum chamber so that a target area can be polished, etched, or otherwise exposed for inspection, which takes place inside the vacuum chamber. Known methods of surface delayering include mechanical polishing or abrading the sample, wet chemical deprocessing, or dry etch processing (RIE). All of these ex-situ methods require very precise control of every step involved in the process in order to ensure accurate results. Generally, these methods are directed to global delayering or removing layers from the entire sample surface. Additionally, monitoring of the delayering process and target area inspection requires frequent and time-consuming transfer of the sample from the SEM chamber to another location for processing and then transfer back to the SEM chamber for monitoring and inspection. The process is time consuming and requires a high level of skill to produce reliable end results. If the process does not produce the desired results then the process may have to be repeated until the desired results are achieved. Even with the high level of skill involved the process typically produces a non-uniform surface of the sample which interferes with the failure analysis. Furthermore, the process leads to contamination of the target area because of residual debris and/or contaminants, such as, for example, abrasive slurry or chemical products used in the delayering process.

Another known method of surface delayering uses a focused ion beam (FIB). One benefit of FIB delayering is that it is typically conducted in-situ or within the vacuum chamber so that the sample does not have to be removed and taken to another location for processing. In a typical FIB delayering process, a target area is exposed using a focused ion beam. Typical FIB techniques use a low level of current remove an area of material from a wafer surface. Various FIB techniques are known. For example, one FIB technique may use less than about 1,000 picoamperes (pA) to expose a target area of about 15 micron ($\mu m$)×15 $\mu m$. One problem with this and other FIB techniques is that they are time consuming due to the low level current, which can be on the order of about thirty minutes. Additionally, surface delayering by FIB often results in a non-uniform surface. A non-uniform surface prevents good ohmic contact between the probe and sample surface because the contact between the probe and the electrical circuit is not of sufficient quality and prevents measuring the desired electrical property of the electrical circuit as needed for fault isolation. For example, with FIB delayering the surfaces of the sample structure often consist of different materials and typically contain copper structures. The various materials have different mill rates which can be one cause of non-uniformity of the delayered surface. Another cause of non-uniform surfaces is that the copper structures are typically polycrystalline with some grain oriented in channeling directions. Once a non-uniform surface is created, further delayering exacerbates the surface non-conformity, especially for the layer where no inherent etch stop layer exists. One example of an undesirable non-uniform sample surface resulting from FIB delayering is shown in FIG. 1. A sample 100 is shown with a region 102 exposing a delayered surface 104. Here, it can be seen that the delayered surface 104 of the sample 100 is non-uniform in depth exposing some electrical circuitry while other circuitry is etched away or is unreachable by the probe. This results in a sample that is not useful for fault isolation.

Other in-situ work piece processing methods are known, such as, for example, repair of defects in lithographic photo-masks and semiconductors. One such method is shown in described in U.S. Pat. No. 7,375,324, to Linder et al, for "Stylus System for Modifying Small Structures." This method repairs defects of the type that lie above the sample surface. In this method, a probe having a cross section of about 0.2 $\mu m$ or less is scanned horizontally across the surface of a sample. At various locations, the probe is stopped and lowered until it contacts the sample surface. The height at which the probe tip stops is measured by circuitry.

The probe tip is then retracted and moved to another predetermined location at which the height is again measured. A series of such measurements are conducted to provide a profile or topography of the sample to locate the defect. Once the defect is located, the probe tip is brought into contact with the defect material and the probe tip is moved in a back-and-forth manner called dithering to cause small fractures in the defect material which breaks up the defect into fragments that are then pushed away from the upper surface of the sample. However, this method and apparatus is used for repairing defects and is not capable of delayering a sample surface for fault analysis.

What is needed is an apparatus and method that overcomes the problems of prior known methods of preparing a sample for fault analysis by eliminating time consuming ex-situ processing steps. What is also needed is an apparatus and method of preparing a sample for fault analysis that is free of contamination and debris. Furthermore, what is further needed is an apparatus and method that is free of problems of known in-situ processing steps by providing a target area of a sample having a clean and uniform surface.

SUMMARY OF THE INVENTION

An object of the invention, therefore, is to provide a method of in-situ surface delayering of a sample resulting in a clean and uniform surface for fault analysis.

The present invention provides a method and apparatus for use in fault isolation and defect localization of a sample work piece in the semiconductor industry, and more particularly to a method and apparatus for mechanically removing or peeling one or more layers from the sample in a rapid, controlled, and accurate manner. According to the present invention, the surface delayering may take place inside a chamber, such as, for example, a vacuum chamber, so that the target area of the sample can be observed in-situ with FIB/SEM imaging.

In a preferred embodiment, the present invention provides a specialized delayering probe tip that is shaped to quickly and accurately peel away a layer of material from a sample having multiple layers. According to a preferred embodiment of the invention, the delayering probe tip is connected to and controlled by an actuator. The delayering probe tip is moved into contact with the surface of a sample at a predetermined location and a force is applied to the delayering probe tip as it is moved across the sample surface to peel away one layer of material at a time to reveal an underlying layer of the sample so that the underlying layer can be observed and analyzed.

According to another aspect of the invention, the delayering probe tip has a cutting face configured so that the lateral shape and size of each individual cut or peeled area of the sample is determined by the lateral size and shape of the delayering probe tip cutting face. The delayering probe tip may be moved across the sample surface one or more times making individual cuts in the sample surface to provide an area of a predetermined size necessary for observation and analysis.

In another aspect of the invention, in-situ surface delayering allows imaging using FIB/SEM. When a fault occurs it is not clear what caused the failure or where in the sample the failure occurs. Preliminary determination can be made according to what type of fault occurs so that the delayering probe tip can be moved by the actuator to the general location at which it is suspected that the fault occurred. The Z-force or vertical force applied to the delayering probe tip can be varied according to the location on the sample. Imaging allows an operator to know about how much force to apply to the probe tip so that, for example, more force can be applied on peaks of surface non-uniformities.

The foregoing has outlined rather broadly the features and technical advantages of the present invention in order that the detailed description of the invention that follows may be better understood. Additional features and advantages of the invention will be described hereinafter. It should be appreciated by those skilled in the art that the conception and specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a more thorough understanding of the present invention, and advantages thereof, reference is now made to the following descriptions taken in conjunction with the accompanying drawings, in which.

DETAILED DESCRIPTION OF PREFERRED EMBODIMENTS

The present invention provides a method and apparatus for preparing a sample for fault isolation and defect localization in order to conduct failure analysis using electrical probing. More specifically, this invention provides a method and apparatus for delayering a sample for fault isolation and defect localization within a vacuum chamber so that inspection may be performed using FIB/SEM imaging, although other tools may be employed. The method of the present invention may be performed without removing the sample from the chamber.

The present invention eliminates ex-situ steps for delayering a sample and utilizes a FIB/SEM chamber for the delayering steps in-situ. The delayering can be monitored using high FIB/SEM-precision at any time during the delayering process. This eliminates the usual dependencies and uncertainties due to changed external conditions or sample properties from which conventional methods suffer, such as, for example, contamination, residual debris, and oxidation from exposure to ambient atmosphere.

A preferred embodiment of the invention provides a method and apparatus for delayering a sample for fault isolation and defect localization. The sample is placed onto a support within a vacuum chamber and a target area on the sample, believed to be the general location of a failure, is identified. A delayering probe tip is selected and mounted to a programmable actuator. The delayering probe tip has a cutting edge that contacts the sample surface and peels away one or more surface layers from the sample leaving a clean and uniform surface so that an electrical probe can contact the exposed surface for fault analysis. The cutting edge of the delayering probe tip is shaped and configured to remove material from the sample so that the lateral dimension of each cut or peeled area is defined by the lateral dimension of the cutting edge of the delayering probe tip. The delayering probe tip is moved into contact with the sample surface at or near the target area and a Z-force is applied to the delayering probe tip sufficient to cut into a first layer of material of the sample. The delayering probe tip is then moved forward in a direction perpendicular to the cutting face to peel away a layer of material from the sample leaving an exposed area having a clean and uniform surface for contact with an electrical probe. This process of peeling away a layer at a time or peeling away a region of a desired size can be repeated until it is determined that a fault has been located.

Figure 1:
FIG. 1 is an image of a delayered region of a sample using FIB.
Figure 2:
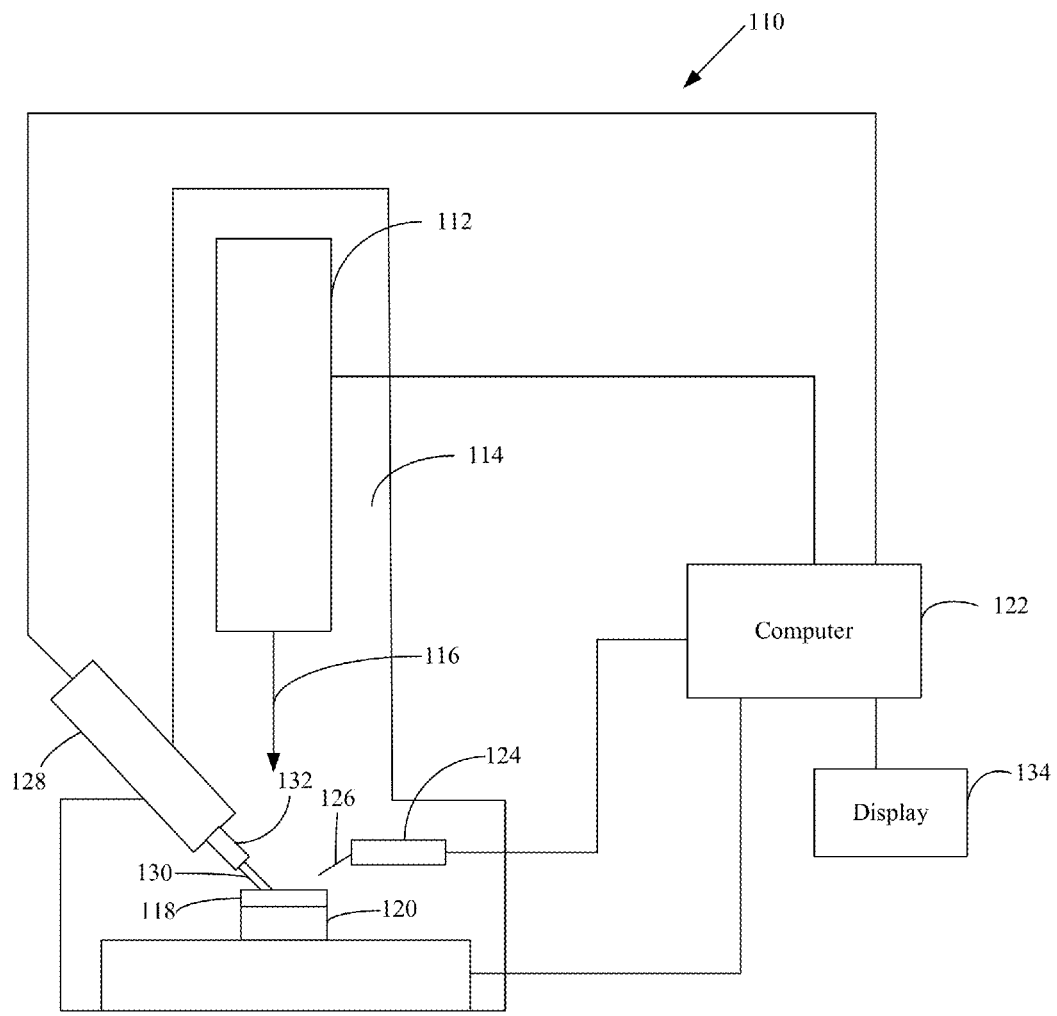
FIG. 2 shows a preferred system for in-situ surface delayering according to the present invention.

FIG. 2 shows a preferred system 110 embodying the present invention. A scanning electron microscope (SEM) 112 or other observation device is provided within a vacuum chamber 114 and is focused along an optical axis 116 onto a sample 118 which will typically have several layers of different materials. Sample 118 is placed onto a support surface of a stage 120 that can move in an X, Y, and Z-axis. Stage 120 can be tilted, if necessary, to provide horizontal two-dimensional and tilt control of sample 118. A computer or controller 122 is connected to SEM device 112 and stage 120 allowing an operator control of the process. An electrical probe 124 having an electrical probe tip 126 is positioned in proximity to sample 118 so that electrical probe tip 126 can be moved into and out of contact with the sample surface for fault analysis. The electrical probe 124 is connected to and controlled through computer 122 by the operator. A programmable actuator 128 is provided for manipulating a delayering probe tip 130. Actuator 128 is connected to and controlled by the operator through computer 122. Delayering probe tip 130 is removably mounted within a chuck or holder 132 and projects downwardly to selectively engage the top surface of sample 118 to peel away a layer of material. A display 134 is connected to computer 122 and provides information to the operator, including an image of sample 118. Delayering probe tip 130 can be moved across the surface of sample 118 in various directions, including horizontal X and Y directions as well as vertical Z direction. Progress of the peeling process can be monitored by live SEM imaging on display 134.

Preferably, delayering probe tip 130 extends downwardly to engage the surface of sample 118 at an angle of 50° or less. For example, delayering probe tip 130 may engage the sample surface in the range of about 45° to about 50°. Once the delayering probe tip 130 is mounted it has some flexibility of movement and can be moved within a limited range of motion of plus or minus about 1 mm in the x-y direction. If a larger range of motion is needed, the delayering probe tip 130 can remain stationary and the sample stage 120 can be moved, if needed.

Figure 3:
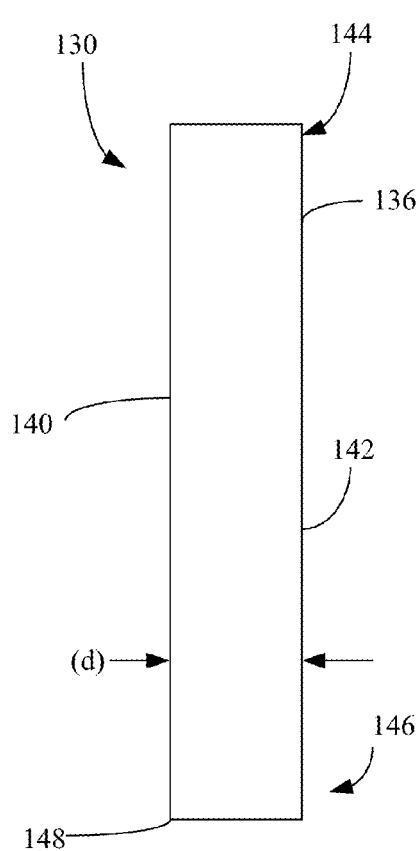
FIG. 3 is a front view of the delayering probe tip.
Figure 4:
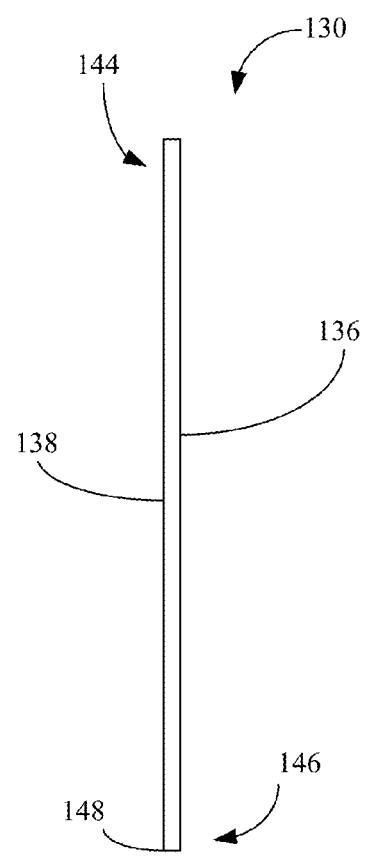
FIG. 4 is a side view of the delayering probe tip.
Figure 5:
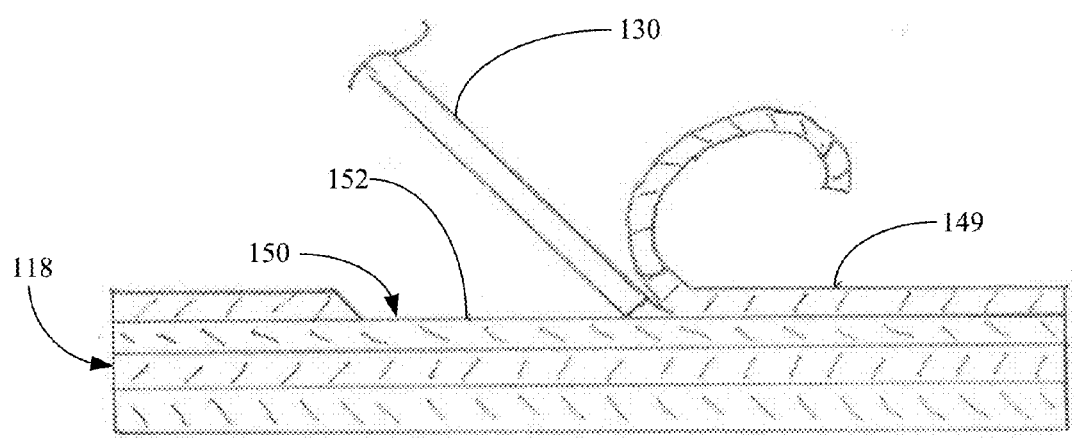
FIG. 5 is a side view showing the delayering probe tip of the present invention delayering a sample.
Figure 6:
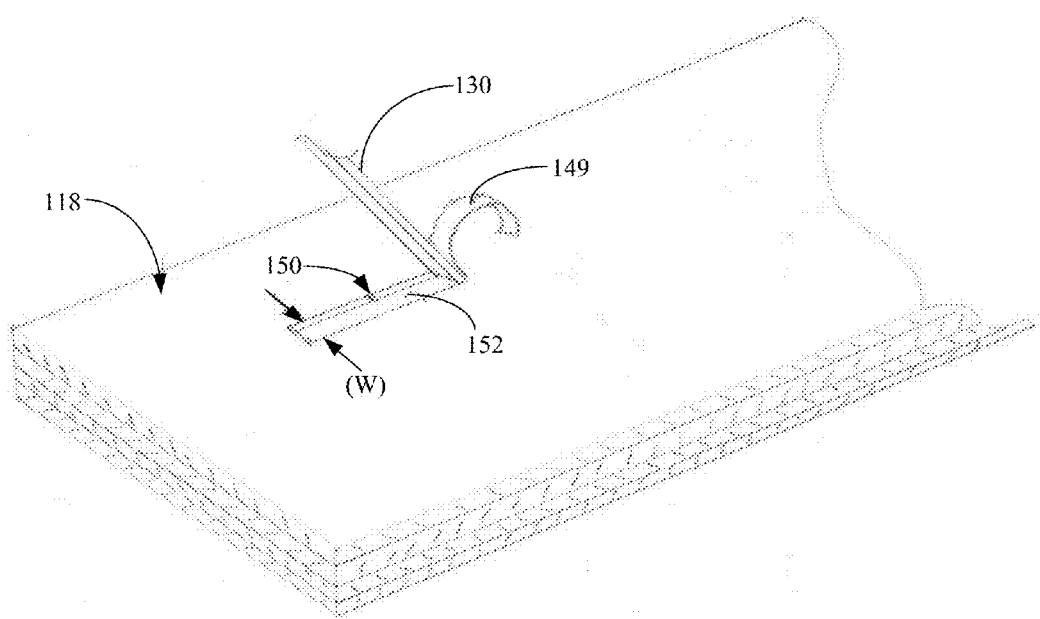
FIG. 6 is another view showing the delayering probe tip of the present invention delayering a sample.

In a preferred embodiment shown in FIGS. 3 and 4, delayering probe tip 130 includes a front side 136, a back side 138, and opposed side edges 140, 142. A proximal end 144 of delayering probe tip 130 is inserted into and held as shown in FIG. 2 by holder 132 of actuator 128. Delayering probe tip 130 is preferably uniform along its length to have a squared off rectangular shape. However, proximal end 144 may be configured as necessary to conform to holder 132 in FIG. 2. Terminal end 146 is squared off to form a sharp linear cutting edge 148. Cutting edge 148 preferably has a width dimension (d) within the range of between about 10 µm to about 50 µm. Although delayering probe tip 130 as shown has a squared configuration with a flat linear cutting edge 148, other shapes and configurations of the cutting edge are contemplated by this invention. For example, the cutting edge may be angled along the probe axis terminating in a sharp point at one side, angled along each side terminating in a central sharp point, or beveled. Preferably, delayering probe tip 130 is made of metal, such as, for example, tungsten. However, other metals or materials may be used. As can be seen in FIGS. 5 and 6, when cutting edge 148 is positioned against the surface of sample 118 and a Z-force is applied, delayering probe tip 130 is moved forward in a direction perpendicular to cutting edge 148 to peel away of a layer 149 of material. The resulting cut or peeled area 150 in sample 118 has a width dimension (w) that is substantially the same as the width dimension (d) of cutting edge 148. The length of peeled area 150 is variable and is determined by the operator so as to reveal enough of a clean and uniform surface 152 of the target area to be probed by electrical probe 124.

Delayering of the sample surface may occur through various steps. For example, if the target area or the suspected location of the fault is relatively certain, delayering probe tip 130 may be actuated to produce one cut or peel at a time at the same location exposing an underlying layer with each peel. Electrical probing may be conducted between each peel until the fault is confirmed. Once the fault is confirmed the delayering process is ended. Alternatively, two or more cuts or peels may be conducted at each layer in order to expose a larger area of the underlying layer before electrical probing.

Figure 7:
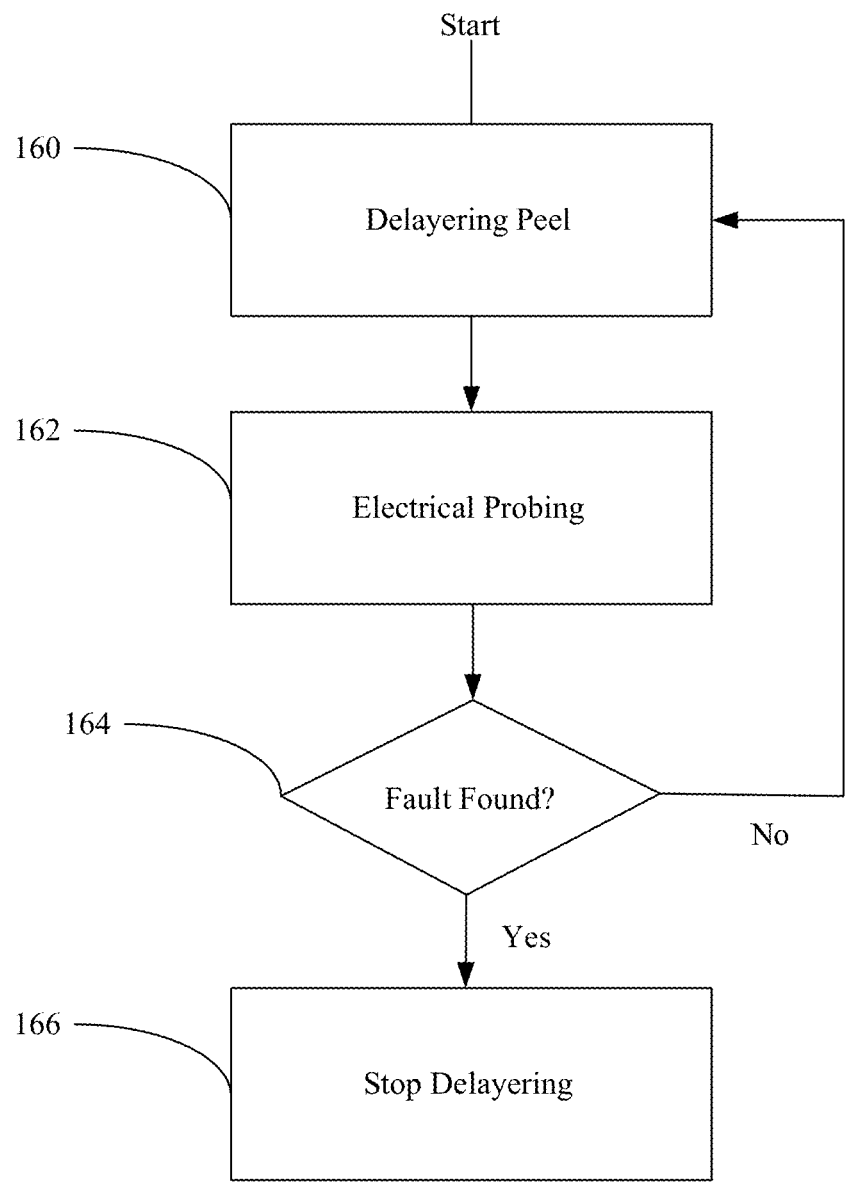
FIG. 7 is a flow chart illustrating the method of delayering a sample for fault isolation and analysis.

In one method of performing a surface delayering and fault isolation according to the invention is seen in FIG. 7. The method involves the use of the system 110 as shown and described in FIGS. 2-6. To start, a sample 118 is mounted on movable stage 120 of within vacuum chamber 114 and aligned so that the target area of sample 118 is aligned with beam axis 116 for imaging of the sample. Then, a delayering step 160 may be conducted to remove or peel away one layer to expose a clean and uniform surface 152 on the underlying layer. The delayering step 160 may include making a single cut or peel for each layer or may include making two or more cuts or peels at the same layer to expose a larger surface area of the underlying layer. An electrical probing step 162 is then performed in which electrical probe tip 126 is moved into contact with exposed surface 152. An electrical current or voltage is applied to the sample surface determine if the target area is the location of the fault. If a fault is found in step 164 at the exposed layer the delayering process is ended 166. If no fault is found, the delayering process is repeated. The next exposed surface is electrically probed in the same manner and if a fault is found the delayering process is ended. If no fault is found the delayering and electrical probing steps are repeated until the fault is found and the delayering process is ended.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the

We claim as follows:

1. An apparatus for in-situ delayering of a sample for fault isolation and defect localization, comprising:
   an optical device for producing a beam along an optical axis;
   a vacuum chamber;
   a motion stage located with the vacuum chamber for supporting a sample for surface delayering, the motion stage being movable relative to the optical axis; and
   an actuator having a delayering probe tip for removing a layer of material from a surface of the sample, wherein the delayering probe tip includes a cutting edge to engage the sample surface and peel away strips of material from the surface of the sample as the probe tip moves across the sample surface in a direction perpendicular to the cutting edge to reveal an underlying layer to locate a defect beneath the surface of the sample for analysis.

2. The apparatus of claim 1, wherein the delayering probe is located to perform surface delayering within the vacuum chamber while being observed by the optical device.

3. The apparatus of claim 1, wherein the delayering probe tip includes a cutting edge capable of peeling away material from the surface of the sample.

4. The apparatus of claim 1, wherein the cutting edge creates a peeled area on the sample, wherein the peeled area has a width dimension defined by the cutting edge of the delayering probe tip.

5. The apparatus of claim 1, wherein the delayering probe tip has a width dimension and is formed to peel away an area on the sample, wherein the peeled area on the sample has a width dimension that is substantially equal to the width dimension of the delayering probe tip.

6. The apparatus of claim 1, wherein the cutting edge of the delayering probe tip has a width dimension of 50 µm or less.

7. The apparatus of claim 6, wherein the width dimension of the cutting edge is within the range of 10 µm to 50 µm.

8. The apparatus of claim 1, wherein the delayering probe tip is mounted within the actuator to contact the surface of the sample at an angle of 50° or less.

9. The apparatus of claim 8, wherein the delayering probe tip is mounted within the actuator to contact the surface of the sample within the range of between 45° to 50°.

10. The apparatus of claim 1, wherein the delayering probe tip is made of tungsten.

11. A method of in-situ delayering of a sample for fault isolation and defect localization, comprising the steps of:
   providing an optical device for producing a beam along an optical axis;
   providing a vacuum chamber;
   providing a motion stage located with the vacuum chamber for supporting a sample for surface delayering, the motion stage being movable relative to the optical axis;
   providing an electrical probe for establishing electrical contact with the sample; and
   providing an actuator having a delayering probe tip with a cutting edge for removing a layer of material from a surface of the sample, wherein the step of removing a layer of material from the sample includes peeling away the layer in strips by moving the probe tip across the sample surface in a direction perpendicular to the cutting edge to expose an underlying layer surface to locate a defect beneath the surface of the sample for analysis.

12. The method of claim 11, wherein the step of removing a layer of material from the sample includes peeling away the layer to expose an underlying layer surface.

13. The method of claim 11, wherein the step of removing a layer of material from the sample includes peeling away an area of the sample wherein the area has a width dimension defined by a width dimension of the delayering probe tip.

14. The method of claim 11, wherein the cutting edge of the delayering probe tip is formed a width dimension of 50µm or less.

15. The method of claim 11, further comprising the step of removing a layer of material from the sample in which the delayering probe tip contacts the sample surface at an angle of 50° or less.

16. The method of claim 11, wherein the delayering probe tip is formed from tungsten.

17. The method of claim 11, wherein the steps of delayering a sample include
   peeling away a layer of material from the sample to expose a surface of an underlying layer;
   electrical probing of the exposed surface to determine a location of an electrical failure; and
   stopping the delayering process if a failure is found or continuing the delayering and electrical probing steps until a failure is located.

* * * * *